US011013706B2

(12) United States Patent
Shen et al.

(10) Patent No.: US 11,013,706 B2
(45) Date of Patent: May 25, 2021

(54) **NON-PHARMACEUTICAL BACTERICIDAL COMPOSITION AGAINST *HELICOBACTER PYLORI***

(71) Applicant: ECO-GEO BIO-TECHNOLOGY COMPANY LIMITED., Taipei (TW)

(72) Inventors: Ta-Lu Shen, Taipei (TW); Fu-An Chen, Taipei (TW)

(73) Assignee: ECO-GEO BIO-TECHNOLOGY COMPANY LIMITED., Taipei (TW)

(*) Notice: Subject to any disclaimer, the term of this patent is extended or adjusted under 35 U.S.C. 154(b) by 0 days.

(21) Appl. No.: 16/992,707

(22) Filed: Aug. 13, 2020

(65) Prior Publication Data

US 2021/0093596 A1    Apr. 1, 2021

Related U.S. Application Data

(62) Division of application No. 16/683,419, filed on Nov. 14, 2019.

(30) Foreign Application Priority Data

Sep. 27, 2019 (TW) ................................ 108135302

(51) Int. Cl.
*A61K 31/194* (2006.01)
*A61K 9/00* (2006.01)
*A61K 31/375* (2006.01)

(52) U.S. Cl.
CPC .......... *A61K 31/194* (2013.01); *A61K 9/0056* (2013.01); *A61K 31/375* (2013.01)

(58) Field of Classification Search
CPC combination set(s) only.
See application file for complete search history.

(56) References Cited

U.S. PATENT DOCUMENTS

| 4,384,005 A | 5/1983 | McSweeney |
| 2010/0151104 A1 | 6/2010 | Smith |

FOREIGN PATENT DOCUMENTS

JP          11137171         5/1999

OTHER PUBLICATIONS

Zazgornik (Wien Klin Wochenschr, 2011, 123: 38-40) (Year: 2011).*
Tadjrobehkar et al. (IJMS, vol. 29, 2, Jun. 2004). (Year: 2004).*
Dunne, C. et al. "Factors That Mediate Colonization of the Human Stomach by Helicobacter Pylori" May 21, 2014. World Journal of Gastroenterology 20(19): 5610-5624.
Sarosiek, J. et al. "Breakdown of the mucus layer by H. pylori" (1994) H. Pylori—Basic Mechanisms to Clinical Cure, 123-128.
"Quadruple Therapy With Bismuth Can Increase the Bactericidal Rate of Helicobacter Pylori!" (2017).
Debraekeleer, A. and Remaut, H. "Future Perspective for Potential Helicobacter Pylori Eradication Therapies" (2018) Future Microbiology 13(6): 671-687.
Allen, A. and Flemstrom, G. "Gastroduodenal Mucus Bicarbonate Barrier: Protection Against Acid and Pepsin" (2005) Am J Physiol Cell Physiol 288: C1-C19.
Scott, D. et al. "The Life and Death of Helicobacter Pylori" Gut 1998;43 (suppl 1): S56-S60.
Suiryanrayna, M. and Ramana, J.V. "A Review of the Effects of Dietary Organic Acids Fed to Swine" Suiryanrayna and Ramana Journal of Animal Science and Biotechnology (2015) 6:45, 1-11.
Marshall B.J. et al. "Urea Protects Helicobacter (Campylobacter) Pylori From the Bactericidal Effect of Acid" Gastroenterology 1990; 99: 697-702.
Clyne, M. "Helicobacter Pylori Requires an Acidic Environment to Survive in the Presence of Urea" Infection and Immunity, May 1995, p. 1669-1673.
Garner, A. "Gastric Mucosal Protective Mechanisms: Roles of Epithelial Bicarbonate and Mucus Secretions" Scand J Gastroenterol Suppl. 1984;101:79-86. (Abstract).
Kauffman, G.L. Jr. "Gastric Mucus and Bicarbonate Secretion in Relation to Mucosal Protection" J Clin Gastroenterol. 1981;3(Suppl 2):45-50. (Abstract).
Shiotani, A. "Citric Acid-Enhanced Helicobacter Pylori Urease Activity In Vivo is Unrelated to Gastric Emptying" . Aliment Pharmacol Ther 2001; 15: 1763-1767.
Jampilek, J. and Kralova, K., "Bactericidal Activity" in Goldman's Cecil Medicine (Twenty Fourth Edition), 2012.
Nozawa, S.R. "Mind the Buffering Capacity of Citric Acid" Fungal Genetics Reports: vol. 42, Article 16 (1995).
Agha, A. "Effect of Different Organic Acids (Citric, Malic and Ascorbic) on Intragastric Urease Activity". Aliment Pharmacol Ther 2005; 21:1145-1148.
Odum, L. and Andersen, L.P. "Investigation of Helicobacter Pylori Ascorbic Acid Oxidating Activity" FEMS Immunology and Medical Microbiology, 10(1995) 289-294.
Celli, J.P. et al. "Helicobacter Pylori Moves Through Mucus by Reducing Mucin Viscoelasticity" PNAS, 106: 34,14321-14326 (2009).
Wheeler, M.H. "Progress Report: Inhibition of Gastric Secretion by the Pyloric Antrum". Gut, 1974, 15, 420-432.
Phillipson, M. "Acid Transport Through Gastric Mucus" (2004) Upsala Journal of Medical Sciences, 109:1, 1-24.
McLauchlan, G. et al. "Comparison of Gastric Body and Antral PH: A 24 Hour Ambulatory Study in Healthy Volunteers" Gut, 1989, 30, 573-578.
Vidyasagar, S. et al. "Three Distinct Mechanisms of HCO3 Secretion in Rat Distal Colon" (2004) Am J Physiol Cell Physiol 287: C612-C621.
Aditi, A. and Graham, D.Y."Vitamin C, Gastritis, and Gastric Disease: A Historical Review and Update" Dig Dis Sci. Oct. 2012; 57(10).
Pillai, K. et al. "Mucolysis by Ascorbic Acid and Hydrogen Peroxide on Compact Mucin Secreted in Pseudomyxoma Peritonei". J Surg Res. May 15, 2012;174(2):e69-73.
Jaka, H. et al."Helicobacter Pylori Mutations Conferring Resistance to Fluoroquinolones and Clarithromycin among Dyspeptic Patients Attending a Tertiary Hospital, Tanzania" Canadian Journal of Gastroenterology and Hepatology, vol. 2019.

(Continued)

*Primary Examiner* — Umamaheswari Ramachandran
(74) *Attorney, Agent, or Firm* — Volpe Koenig

(57) ABSTRACT

The present invention provides a non-pharmaceutical bactericidal composition against a *Helicobacter pylori*, including a first daily edible component and a second daily edible component.

7 Claims, 4 Drawing Sheets

(56) References Cited

OTHER PUBLICATIONS

"Causes and Countermeasures for the Failure of Helicobacter Pylori Eradication" (2006)16(5), 276-282.
Zawilak-Pawlik, A. and Zakrzewska-Czetwhiska, J. "Molecular Pathogenesis and Signal Transduction by Helicobacter pylori" (2017).
Zhang, H.M. et al. "Vitamin C Inhibits the Growth of a Bacterial Risk Factor for Gastric Carcinoma: Helicobacter pylori" (1997) Cancer 80(10): 1897-1903.
Zone of Inhibition Test for Antimicrobial Activity, Aug. 8, 2016.
Kauffman, G.L. "Gastric mucus and bicarbonate secretion in relation to mucosal protection." (1981) J Clin Gastroenterol 3(Suppl 2): 45-50 Abstract.
New Human Physiology | Paulev-Zubieta 2nd Edition, Chapter 17: The Acid-Base Balance and Disorders, 1999.
Zhang, L. et al. "Efficacy of Cranberry Juice on Helicobacter pylori Infection: a Double-Blind, Randomized Placebo-Controlled Trial" (2005) Helicobacter 10(2): 139-145.
Khomych, G. et al. "Study of the Chemical Composition of Cranberry and the Use of Berries in Food Technology" (2017) Eastern European Journal of Enterprise Technologies 6(11): 59-65.

\* cited by examiner

NON-PHARMACEUTICAL BACTERICIDAL COMPOSITION AGAINST *HELICOBACTER PYLORI*

CROSS-REFERENCED TO RELATED APPLICATION AND CLAIM OF PRIORITY

This application is a divisional of U.S. patent application Ser. No. 16/683,419, filed on Nov. 14, 2019, which claims the benefit of Taiwan Patent Application No. 108135302, filed on Sep. 27, 2019, at the Taiwan Intellectual Property Office, which are incorporated herein by reference as if fully set forth.

FIELD OF THE INVENTION

The present invention refers to a non-pharmaceutical bactericidal composition against *Helicobacter pylori*, specifically to a non-pharmaceutical bactericidal composition against *Helicobacter pylori* for performing the functions of killing the *Helicobacter pylori* and inhibiting the ascorbate oxidase activity of the *Helicobacter pylori* in an environment below pH5.

BACKGROUND OF THE INVENTION

Global *Helicobacter pylori* infection rate exceeds 50% of the global population, and 10%-15% of those infections result in the development of peptic ulcer diseases. *Helicobacter pylori* is associated with 95% of duodenal ulcers and 80% of gastric ulcers. 1%-3% of infected individuals develop gastric cancer. Therefore, *Helicobacter pylori* is classified by the World Health Organization (WHO) as a primary carcinogen (please refer to D(1)).

In recent years, studies of the survival and pathogenesis of *Helicobacter pylori* in gastric mucus are the foci of the medical community to observe the microbial pathogenesis (chronic infections) in mucus in general. The medical community hopes to work out a solution to eliminate other toxic pathogenic microorganisms in mucus in general via eliminating *Helicobacter pylori* effectively in the mucus, as intestinal dysbiosis is often the cause of some chronic diseases such as obesity, diabetes and inflammatory diseases (please refer to D(1)).

*Helicobacter pylori* is one of the most interesting microorganisms in the human digestive tract, and is associated in particular with active inflammatory changes within the gastroduodenal mucus (about 50-65% with the gastric ulcer and about 95% with the duodenal ulcer). According to research, *Helicobacter pylori* infected persons should eliminate *Helicobacter pylori* completely to avoid ulcer recurrence and ulcer complications (please refer to D(2)).

*Helicobacter pylori* is a smart bacterium that can coexist peacefully with the human host once it resides in the stomach of a human body. Clinically, it was found that 80% to 90% of persons infected with *Helicobacter pylori* have chronic gastritis, but only 20% of them show symptoms; 15% to 20% of the infected persons develop gastric ulcer or duodenal ulcer, 1% to 3% of carriers of *Helicobacter pylori* develop gastric cancer, and one in one thousand to one in ten thousand of them have gastric lymphoma problems. Compared with someone uninfected by *Helicobacter pylori*, the risk of developing stomach cancer of the infected persons is increased by 6 times (please refer to D(3)).

Recent evidence suggests that prolonged colonization of the gastric mucus by *Helicobacter pylori* may lead to chronic atrophic gastritis and subsequently adenocarcinoma (please refer to D(2)).

Future perspectives for therapies of *Helicobacter pylori* can be discussed in the following aspects (1) to (3) (please refer to D(4)):
(1) The bottlenecks of today's therapy in general:
   A rising antibiotic resistance of *Helicobacter pylori*
   Health concerns over long-term use (a course of 10-14 days, 3 to 4 times per day)
   High single dosage required due to antibiotic resistance (500 to 1000 mg of a single antibiotic treatment)
   A rising recurrence
   Other complications induced by antibiotics include:
      a. obesity
      b. fatty liver disease
      c. Type 2 diabetes
   The expected primary effect of antibiotics is significantly affected and reduced by the presence of the gastric mucus, which results in enhanced side effects such as the liver, kidney and stomach damages due to the increase of dosage to compensate for the reduction of the intended primary effect.
   The adverse effects of antibiotics may lead to discomfort of the patients.
*The patients having cancer attributable solely to *Helicobacter pylori* infection (780,000 cases) account for 6.2%, a very high proportion, of all cancers yearly worldwide.
(2) Some advanced versions of traditional "triple therapy" nowadays:
   Bismuth is sometimes added to become "quadruple therapy" and to increase the therapeutic effect, and the main effect of bismuth is to inhibit the urease activity.
   N-acetylcysteine (NAC) replaces bismuth to be added into the triple therapy, or to be used alone.
   Main side effects of the NAC:
      a. It has a high toxicity and needs to be used in a high dosage.
      b. It reduces the viscosity of the gastric mucus effectively but tends to cause ulcer deterioration as well.
(3) Latest research and development directions for the therapy of *Helicobacter pylori* infection:
   narrow-spectrum
   non-antibiotic

*Helicobacter pylori* mainly colonizes the human antrum mucosa (please refer to FIG. 1 in D(1)). The pH values in the gastric mucus naturally form a pH-gradient. The main cause is that the apical portion of the epithelial cells secretes bicarbonate ($HCO_3^-$) into the mucus to fight against the acid attack from the gastric lumen (please refer to the abstract in D(5)). Therefore, the composition of the present invention must be able to fight against alkali (i.e. bicarbonate ($HCO_3^-$)) in the gastric mucus and sterilize bacteria in a low pH mucus-microenvironment created by this composition. Furthermore, gastric juice contains urea, and *Helicobacter pylori* will hydrolyze the urea there to raise the pH value of the microenvironment while the ambient pH is low. Generally, antibiotics are active between pH 5-8, so they need to be taken in combination with an antacid or a Proton Pump Inhibitor (PPI) to neutralize the gastric acid or inhibit gastric acid secretion to avoid low pH in the stomach which causes deactivation of antibiotics (please refer to FIG. 3 in D(6)). In summary, the bicarbonate ($HCO_3^-$) in the gastric mucus is vital for the colonization of *Helicobacter pylori*. In addition, the urease there is also another crucial factor that helps *Helicobacter pylori* colonize the gastric mucus.

The "bicarbonate barrier" in the gastric antral mucus gel layer is described in detail as follows:
The colonization of the *Helicobacter pylori* in the gastric antral mucus gel layer is shown in FIG. 1 in D(1).

Regarding the pH-gradient in the gastric antral mucus gel layer, please refer to the abstract in D(5). According to D(5), the characteristics of the "bicarbonate barrier" of the gastric mucosa include a pH-gradient (the pH value varies from low to high from the gastric lumen to the apical portion of the epithelial cells), a resistance to acid, and a resistance to pepsin. In the in vivo experiment in rats on page C6, FIG. 2 in D(5), group A used pentagastrin to stimulate gastric parietal cells to secrete gastric juice, and group B used ranitidine to inhibit gastric acid secretion. Regarding the pH changes in the mucoepithelial interface, a rapid decrease in pH from 7 to 2-3, when the gastric acid secretion is inhibited temporarily, and a bounce back to 6-7 after about 20 minutes were observed in group B. On Page C6, right Column, Lines 4-20 in D(5), it clearly stated that the substances having molecular weight (Da) less than 400, include ions like hydrogen ion and small-sized molecules, are proved by in vivo experiments that they are free to pass through the mucus. Therefore, the main interfering factor which provides the prevention of acid attack in the mucus-microenvironment should be bicarbonate ($HCO_3^-$).

Therefore, for the effective elimination of *Helicobacter pylori* in the stomach, it is crucial to find a composition that is able to fight against bicarbonate ($HCO_3^-$) in the gastric mucus and sterilize bacteria at the same time in such a low pH mucus-microenvironment created by this composition (please refer to FIG. 1 and page 4/11, right Column, Lines 8-20 in D(7) regarding the organic acid kills Gram-negative bacteria including *Helicobacter pylori*).

SUMMARY OF THE INVENTION

One aspect of the present invention is to provide a non-pharmaceutical bactericidal composition against a *Helicobacter pylori*, the non-pharmaceutical bactericidal composition includes a first daily edible component, a second daily edible component, a salt and a third daily edible component, wherein the first daily edible component has a molecular state and a dissociated state while in an aqueous solution state, the first daily edible component of the molecular state is used for performing functions of killing the *Helicobacter pylori* and inhibiting an ascorbate oxidase activity of the *Helicobacter pylori* in an environment with a pH value below 5, and the first daily edible component is a citric acid, a malic acid or a combination thereof, wherein the second daily edible component is used for neutralizing a bicarbonate and being a citric acid, a malic acid or a combination thereof, wherein the salt is used to form a buffer combination with the citric acid, the malic acid or the combination thereof, the salt is a salt of the citric acid, a salt of the malic acid or a combination thereof, and wherein the third daily edible component is used for killing the *Helicobacter pylori* more thoroughly in presence of the first daily edible component, the second daily edible component and the salt, and the third daily edible component is an ascorbic acid.

Another aspect of the present invention is to provide a non-pharmaceutical bactericidal composition against a *Helicobacter pylori*, the non-pharmaceutical bactericidal composition includes a first daily edible component and a second daily edible component, wherein the first daily edible component is a buffer combination consisting of an organic acid and a salt of the organic acid, the first daily edible component is used for neutralizing a bicarbonate and performing functions of killing the *Helicobacter pylori* and inhibiting an ascorbate oxidase activity of the *Helicobacter pylori* in an environment with a pH value below 5, and the organic acid is a citric acid, a malic acid or a combination thereof, and wherein the second daily edible component is used for killing the *Helicobacter pylori* more thoroughly in presence of the first daily edible component, and the second daily edible component is an ascorbic acid.

A further aspect of the present invention is to provide a non-pharmaceutical bactericidal composition against a *Helicobacter pylori*, the non-pharmaceutical bactericidal composition includes a first daily edible component and a second daily edible component, wherein the first daily edible component has a molecular state and a dissociated state while in an aqueous solution state, the first daily edible component of the molecular state is used for performing functions of killing the *Helicobacter pylori* and inhibiting an ascorbate oxidase activity of the *Helicobacter pylori* in an environment with a pH value below 5, and the first daily edible component is a citric acid, a malic acid or a combination thereof, and wherein the second daily edible component is a salt used to form a buffer combination with the first daily edible component, and used to neutralize a bicarbonate, so that the first daily edible component can continue its killing of the *Helicobacter pylori* effectively and inhibiting the ascorbate oxidase activity of the *Helicobacter pylori*, and the salt is a salt of the citric acid, a salt of the malic acid or a combination thereof.

A further aspect of the present invention is to provide a method for treating a *Helicobacter pylori* infection, the method including steps of providing a non-pharmaceutical bactericidal composition including a first daily edible component and a second daily edible component, and administering the non-pharmaceutical bactericidal composition to a mammal, wherein the first daily edible component has a molecular state and a dissociated state while in an aqueous solution state, the first daily edible component of the molecular state is used for performing functions of killing a *Helicobacter pylori* and inhibiting an ascorbate oxidase activity of the *Helicobacter pylori* in an environment with a pH value below 5, the first daily edible component is a citric acid, a malic acid or a combination thereof, and the second daily edible component is a salt, is used to form a buffer combination with the first daily edible component, and is used to neutralize a bicarbonate, so that the first daily edible component can continue its killing of the *Helicobacter pylori* effectively and inhibiting the ascorbate oxidase activity of the *Helicobacter pylori*, and the salt is a salt of the citric acid, a salt of the malic acid or a combination thereof.

BRIEF DESCRIPTION OF THE DRAWINGS

Other objectives, advantages and efficacies of the present invention will be described in detail below taken from the preferred embodiments with reference to the accompanying drawings.

DETAILED DESCRIPTION OF THE PREFERRED EMBODIMENTS

Figure 1:
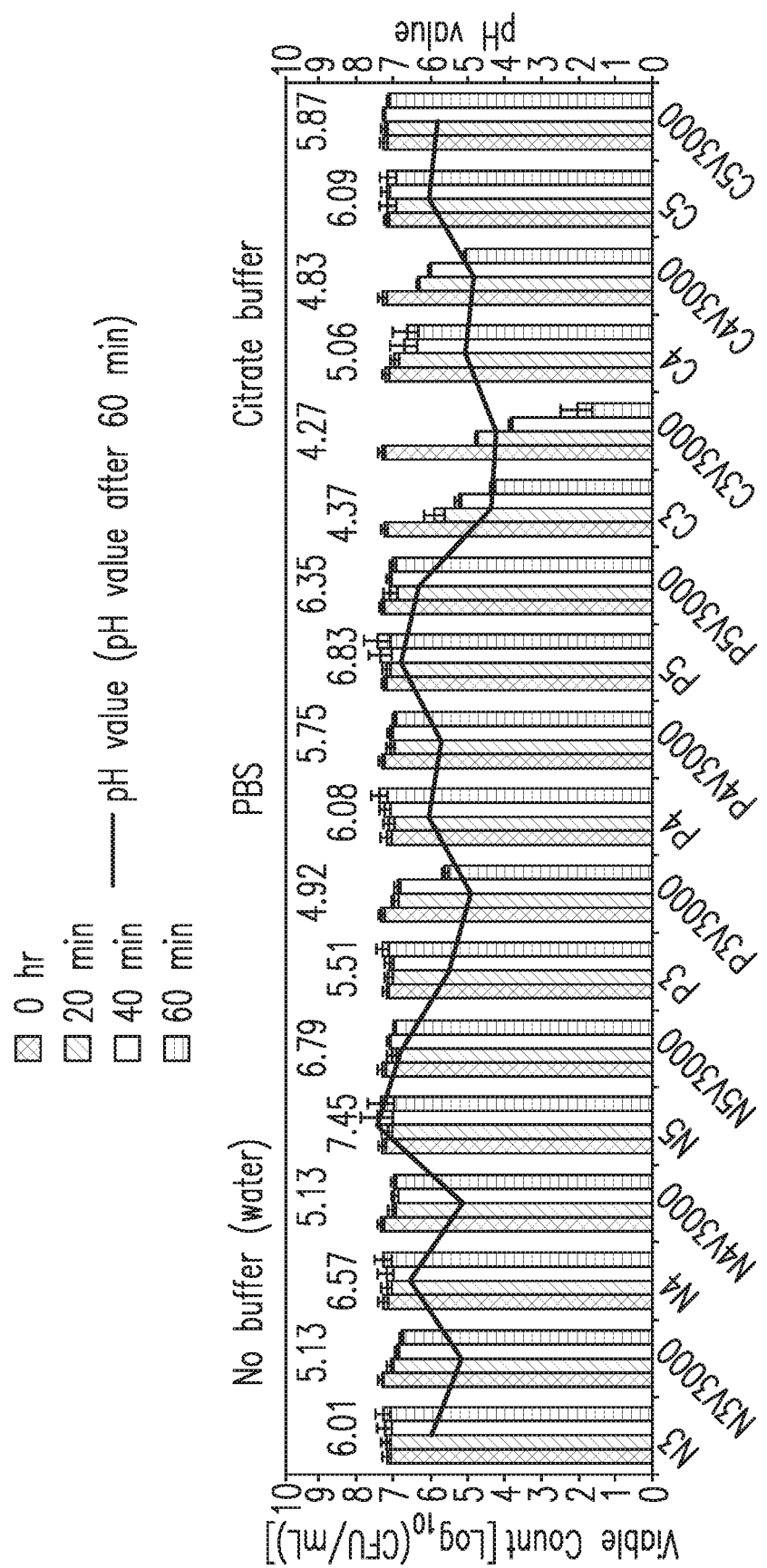
FIG. 1 is a histogram showing the results of an antibacterial experiment against *Helicobacter pylori* of the citrate buffer combination (with or without the ascorbic acid) and a phosphate buffer combination (with or without the ascorbic acid) at pH 3.0, 4.0 and 5.0.

The following are embodiments of the present invention.

I. Experimental Instruments
Autoclave (FD50R, Zealway, USA)
Microcentrifuge (Spectrafuge™ 24D, Labnet, USA)
Electronic Microbalance (XR 205SM-DR, Precisa, Switzerland)
Electronic Balance (PB1502-S, Mettler Toledo, USA)
pH Meter (Delta 320, Mettler Toledo, USA)
Orbital Shaker Incubator (721 SR, HIPOINT, Taiwan)
Biological Safety Cabinets (Ever Win Technology, Taiwan)
Microplate reader (SPECTROstar® Nano, BMG Labtech, Germany)
Water Purification system (Polycon DIU-3, Scienpak Enterprise, Taiwan)
Pipette 10-100 μL (Acura® manual 825, Socorex, Switzerland)
Pipette 20-200 μL (Acura® manual 825, Socorex, Switzerland)
Pipette 100-1000 μL (Acura® manual 825, Socorex, Switzerland)
Serum Bottle 1000 mL (Schott, Germany)
Serum Bottle 500 mL (Schott, Germany)
Serum Bottle 50 mL (Schott, Germany)
Beaker 1000 mL (Kimax, USA)
Beaker 500 mL (Kimax, USA)
Beaker 100 mL (Kimax, USA)
Stirrer (Dogger, Taiwan)
Glass Triangle-headed Cell Spreader (Dogger, Taiwan)
Alcohol Burner (Dogger, Taiwan)
AnaeroPack Jar (MGC AnaeroPack®, Mitsubishi Gas Chemical, Japan)

II. Experimental Consumables
Pipetmen tips 10-200 μL (Vertex®, USA)
Pipetmen tips 100-1000 μL (Vertex®, USA)
Microcentrifuge Tubes 1.5 mL (Jet Biofil®, China)
Centrifuge Tubes 15 mL (Jet Biofil®, China)
Centrifuge Tubes 50 mL (Jet Biofil®, China)
Cell and Tissue Culture Dishes 9.0 cm (Jet Biofil®, China)
Cell and Tissue Culture Plates 48 well (Jet Biofil®, China)
Cell and Tissue Culture Plates 96 well (Jet Biofil®, China)
Syringe Driven Filter 0.22 μm (PVDF membrane, Jet Biofil®, China)
Disposable Syringe 1 mL (Terumo, Japan)
Genbox Microaer (Ref. 96125, bioMerieux, France)

III. Experimental Drugs
Urea (Nihon Shiyaku, Taiwan)
Citric Acid (Nihon Shiyaku, Taiwan)
Sodium Citrate (Nihon Shiyaku, Taiwan)
Potassium Dihydrogen Phosphate (Nihon Shiyaku, Taiwan)
Sodium Hydrogen Phosphate (Nihon Shiyaku, Taiwan)
DL-Malic acid (Shun Ching Raw Material, Taiwan)
Sodium DL-Malate (Gemfont, Taiwan)
Lactic acid (Alfa Aesar, USA)
Sodium Lactate (Hsin Eing, Taiwan)
Sodium hydrogen carbonate (Shimakyu yakuhin, Japan)
Sodium Chloride (Nihon Shiyaku, Taiwan)
Hydrogen Chloride (Nihon Shiyaku, Taiwan)
Sodium Hydroxide (Nihon Shiyaku, Taiwan)
BBL™ *Brucella* broth (BD Biosciences, USA)
Bacto™ Agar (BD Biosciences, USA)
Donor Equine Serum (Hyclone, USA)
L-Ascorbic acid (Sigma, USA)

IV. Experimental Methods

Embodiment 1

The antibacterial experiment against *Helicobacter pylori* of the citrate buffer combination (with or without the ascorbic acid) and a phosphate buffer combination (with or without the ascorbic acid)(viability check-point:0/20/40/60 minutes, triple repetition).

Bacteria Strain and Culturing Method

The bacteria strain used in the experiment was *Helicobacter pylori* strain 26695 (ATCC700392), and the bacteria were subcultured on *Brucella* solid medium (*Brucella* broth 28 g/L, Agar 15 g/L and 10% (v/v) Horse serum, pH 7.0). After the bacteria were seeded by streaking method, they were cultured in a humidified anaerobic chamber at 37° C. for 72 hours using a microaerobic bag (Genbox microaer, BioMerieux, 96125).

Each culture medium was filtered through a 0.22 μm injection type filter for use. *Brucella* broth containing 10 mg/mL of $NaHCO_3$ was added to the *Helicobacter pylori* subcultured for 72 hours, bacterial concentration was adjusted to $10^7$-$10^8$ CFU/mL as a bacterial solution, the bacterial solution was mixed with each culture solution in a 1:1 ratio, and the mixture was incubated at 37° C. in a humidified anaerobic chamber using a micro-aerobic bag (Genbox microaer, BioMerieux, 96125).

The citrate buffer solutions were prepared by mixing the citric acid and sodium citrate in different ratios according to their pH values, and the unmodulable portion was prepared by HCl and NaOH to reach a constant pH value. The phosphate buffer solutions were prepared by mixing $KH_2PO_4$ and $Na_2HPO_4$ in different ratios according to their pH values, and the unmodulable portion was prepared by HCl and NaOH to reach a constant pH value. The pH of the medium was adjusted with HCl and NaOH. After each culture medium was adjusted to a constant pH value using the method above, a constant concentration of ascorbic acid was additionally added to each culture medium. The components of the bacterial solution and each culture medium were as follows:

Bacteria solution: (*Brucella* broth 28 g/L, $NaHCO_3$ 10 g/L and 10 mM urea).

Group 1: N3 (*Brucella* broth 28 g/L and 10 mM urea, pH 3.0).

Group 2: N3V3000 (*Brucella* broth 28 g/L and 10 mM urea, pH 3.0)+(6000 mg/L Vitamin C).

Group 3: N4 (*Brucella* broth 28 g/L and 10 mM urea, pH 4.0).

Group 4: N4V3000 (*Brucella* broth 28 g/L and 10 mM urea, pH 4.0)+(6000 mg/L Vitamin C).

Group 5: N5 (*Brucella* broth 28 g/L and 10 mM urea, pH 5.0).

Group 6: N5V3000 (*Brucella* broth 28 g/L and 10 mM urea, pH 5.0)+(6000 mg/L Vitamin C).

Group 7: P3 (*Brucella* broth 28 g/L, 0.1 M phosphate buffered saline (PBS) and 10 mM urea, pH 3.0).

Group 8: P3V3000 (*Brucella* broth 28 g/L, 0.1 M phosphate buffered saline (PBS) and 10 mM urea, pH 3.0)+(6000 mg/L Vitamin C).

Group 9: P4 (*Brucella* broth 28 g/L, 0.1 M phosphate buffered saline (PBS) and 10 mM urea, pH 4.0).

Group 10: P4V3000 (*Brucella* broth 28 g/L, 0.1 M phosphate buffered saline (PBS) and 10 mM urea, pH 4.0)+(6000 mg/L Vitamin C).

Group 11: P5 (*Brucella* broth 28 g/L, 0.1 M phosphate buffered saline (PBS) and 10 mM urea, pH 5.0).

Group 12: P5V3000 (*Brucella* broth 28 g/L, 0.1 M Phosphate buffered saline (PBS) and 10 mM urea, pH 5.0)+(6000 mg/L Vitamin C).

Group 13: C3 (*Brucella* broth 28 g/L, 0.1 M citrate buffer and 10 mM urea, pH 3.0).

Group 14: C3V3000 (*Brucella* broth 28 g/L, 0.1 M citrate buffer and 10 mM urea, pH 3.0)+(6000 mg/L Vitamin C).

Group 15: C4 (*Brucella* broth 28 g/L, 0.1 M citrate buffer and 10 mM urea, pH 4.0).

Group 16: C4V3000 (*Brucella* broth 28 g/L, 0.1 M citrate buffer and 10 mM urea, pH 4.0)+(6000 mg/L Vitamin C).

Group 17: C5 (*Brucella* broth 28 g/L, 0.1 M citrate buffer and 10 mM urea, pH 5.0).

Group 18: C5V3000 (*Brucella* broth 28 g/L, 0.1 M citrate buffer and 10 mM urea, pH 5.0)+(6000 mg/L Vitamin C).

After each culture medium incubated according to the viability check-point (0/20/40/60 minutes) was serially diluted 10 times with physiological saline, the bacteria solutions diluted at each magnification was applied to the *Brucella* solid medium for subculture by a coating method, and the coated plates were incubated at 37° C. for 72 hours in a humidified anaerobic chamber using a micro-aerobic package (Genbox microaer, BioMérieux, 96125). Finally, the viable count of each culture medium was calculated.

Embodiment 2

The antibacterial experiment against *Helicobacter pylori* of the citrate buffer combination with the ascorbic acid (viability check-point: 0/20/40/60 minutes, triple repetition).

Bacteria Strain and Culturing Method

The bacteria strain used in the experiment was *Helicobacter pylori* strain 26695 (ATCC700392), and the bacteria were subcultured on *Brucella* solid medium (*Brucella* broth 28 g/L, Agar 15 g/L and 10% (v/v) Horse serum, pH 7.0). After the bacteria were seeded by streaking method, they were cultured in a humidified anaerobic chamber at 37° C. for 72 hours using a microaerobic bag (Genbox microaer, BioMerieux, 96125).

Each culture medium was filtered through a 0.22 μm injection type filter for use. *Brucella* broth containing 10 mg/mL of $NaHCO_3$ was added to the *Helicobacter pylori* subcultured for 72 hours, bacterial concentration was adjusted to $10^7$-$10^8$ CFU/mL as a bacterial solution, the bacterial solution was mixed with each culture solution in a 1:1 ratio, and the mixture was incubated at 37° C. in a humidified anaerobic chamber using a micro-aerobic bag (Genbox microaer, BioMerieux, 96125).

The citrate buffer solutions were prepared by mixing the citric acid and sodium citrate in different ratios according to their pH values, and the unmodulable portion was prepared by HCl and NaOH to reach a constant pH value. The phosphate buffer solutions were prepared by mixing $KH_2PO_4$ and $Na_2HPO_4$ in different ratios according to their pH values, and the unmodulable portion was prepared by HCl and NaOH to reach a constant pH value. The pH of the medium was adjusted with HCl and NaOH. After each culture medium was adjusted to a constant pH value using the method above, a constant concentration of ascorbic acid was additionally added to each culture medium. The components of the bacterial solution and each culture medium were as follows:

Group 1: C3V3000 (*Brucella* broth 28 g/L, 0.1 M citrate buffer and 10 mM urea, pH 3.0)+(6000 mg/L Vitamin C).

Group 2: C3V6000 (*Brucella* broth 28 g/L, 0.1 M citrate buffer and 10 mM urea, pH 3.0)+(12000 mg/L Vitamin C).

Group 3: C3V9000 (*Brucella* broth 28 g/L, 0.1 M citrate buffer and 10 mM urea, pH 3.0)+(18000 mg/L Vitamin C).

After each culture medium incubated according to the viability check-point (0/20/40/60 minutes) was serially diluted 10 times with physiological saline, the bacteria solutions diluted at each magnification was applied to the *Brucella* solid medium for subculture by a coating method, and the coated plates were incubated at 37° C. for 72 hours in a humidified anaerobic chamber using a micro-aerobic package (Genbox microaer, BioMerieux, 96125). Finally, the viable count of each culture medium was calculated.

Regarding the details for the addition of urea, please refer to references D(8) and D(9), and regarding the details for the addition of $NaHCO_3$, please refer to references D(6), D(10) and D(11).

Embodiment 3

The antibacterial experiment against *Helicobacter pylori* of the malate buffer combination, the lactate buffer combination, the citrate buffer combination and the phosphate buffer combination (viability check-point: 0/20/40/60 minutes, triple repetition).

Bacteria Strain and Culturing Method

The bacteria strain used in the experiment was *Helicobacter pylori* strain 26695 (ATCC700392), and the bacteria were subcultured on *Brucella* solid medium (*Brucella* broth 28 g/L, Agar 15 g/L and 10% (v/v) Horse serum, pH 7.0). After the bacteria were seeded by streaking method, they were cultured in a humidified anaerobic chamber at 37° C. for 72 hours using a microaerobic bag (Genbox microaer, BioMerieux, 96125).

Each culture medium was filtered through a 0.22 μm injection type filter for use. *Brucella* broth containing 10 mg/mL of $NaHCO_3$ was added to the *Helicobacter pylori* subcultured for 72 hours, bacterial concentration was adjusted to $10^7$-$10^8$ CFU/mL as a bacterial solution, the bacterial solution was mixed with each culture solution in a 1:1 ratio, and the mixture was incubated at 37° C. in a humidified anaerobic chamber using a micro-aerobic bag (Genbox microaer, BioMerieux, 96125).

The citrate buffer solutions were prepared by mixing the citric acid and sodium citrate in different ratios according to their pH values, and the unmodulable portion was prepared by HCl and NaOH to reach a constant pH value. The malate buffer combination and the lactate buffer combination were prepared by mixing malic acid and sodium malate, and lactic acid and sodium lactate, respectively, in the same way. The phosphate buffer solutions were prepared by mixing $KH_2PO_4$ and $Na_2HPO_4$ in different ratios according to their pH values, and the unmodulable portion was prepared by HCl and NaOH to reach a constant pH value. The pH of the medium was adjusted with HCl and NaOH. The components of the bacterial solution and each culture medium were as follows:

Bacteria solution: (*Brucella* broth 28 g/L, $NaHCO_3$ 10 g/L and 10 mM urea).

Group 1: M3 (*Brucella* broth 28 g/L, 0.1 M malate buffer and 10 mM urea, pH 3.0).
Group 2: M4 (*Brucella* broth 28 g/L, 0.1 M malate buffer and 10 mM urea, pH 4.0).
Group 3: M5 (*Brucella* broth 28 g/L, 0.1 M malate buffer and 10 mM urea, pH 5.0).
Group 4: L3 (*Brucella* broth 28 g/L, 0.1 M lactate buffer and 10 mM urea, pH 3.0).
Group 5: L4 (*Brucella* broth 28 g/L, 0.1 M lactate buffer and 10 mM urea, pH 4.0).
Group 6: L5 (*Brucella* broth 28 g/L, 0.1 M lactate buffer and 10 mM urea, pH 5.0).
Group 7: P3 (*Brucella* broth 28 g/L, 0.1 M phosphate buffered saline (PBS) and 10 mM urea, pH 3.0).
Group 8: P4 (*Brucella* broth 28 g/L, 0.1 M phosphate buffered saline (PBS) and 10 mM urea, pH 4.0).
Group 9: P5 (*Brucella* broth 28 g/L, 0.1 M phosphate buffered saline (PBS) and 10 mM urea, pH 5.0).
Group 10: C3 (*Brucella* broth 28 g/L, 0.1 M citrate buffer and 10 mM urea, pH 3.0).
Group 11: C4 (*Brucella* broth 28 g/L, 0.1 M citrate buffer and 10 mM urea, pH 4.0).
Group 12: C5 (*Brucella* broth 28 g/L, 0.1 M citrate buffer and 10 mM urea, pH 5.0).

After each culture medium incubated according to the viability check-point (0/20/40/60 minutes) was serially diluted 10 times with physiological saline, the bacteria solutions diluted at each magnification was applied to the *Brucella* solid medium for subculture by a coating method, and the coated plates were incubated at 37° C. for 72 hours in a humidified anaerobic chamber using a micro-aerobic package (Genbox microaer, BioMerieux, 96125). Finally, the viable count of each culture medium was calculated.

Embodiment 4

The antibacterial experiment against *Helicobacter pylori* of the malate buffer combination with the ascorbic acid, the lactate buffer combination with the ascorbic acid, the citrate buffer combination with the ascorbic acid, and the phosphate buffer combination with the ascorbic acid (viability check-point: 0/20/40/60 minutes, triple repetition).

Bacteria Strain and Culturing Method

The bacteria strain used in the experiment was *Helicobacter pylori* strain 26695 (ATCC700392), and the bacteria were subcultured on *Brucella* solid medium (*Brucella* broth 28 g/L, Agar 15 g/L and 10% (v/v) Horse serum, pH 7.0). After the bacteria were seeded by streaking method, they were cultured in a humidified anaerobic chamber at 37° C. for 72 hours using a microaerobic bag (Genbox microaer, BioMerieux, 96125).

Each culture medium was filtered through a 0.22 μm injection type filter for use. *Brucella* broth containing 10 mg/mL of $NaHCO_3$ was added to the *Helicobacter pylori* subcultured for 72 hours, bacterial concentration was adjusted to $10^7$-$10^8$ CFU/mL as a bacterial solution, the bacterial solution was mixed with each culture solution in a 1:1 ratio, and the mixture was incubated at 37° C. in a humidified anaerobic chamber using a micro-aerobic bag (Genbox microaer, BioMerieux, 96125).

The citrate buffer solutions were prepared by mixing the citric acid and sodium citrate in different ratios according to their pH values, and the unmodulable portion was prepared by HCl and NaOH to reach a constant pH value. The malate buffer combination and the lactate buffer combination were prepared by mixing malic acid and sodium malate, and lactic acid and sodium lactate, respectively, in the same way. The phosphate buffer solutions were prepared by mixing $KH_2PO_4$ and $Na_2HPO_4$ in different ratios according to their pH values, and the unmodulable portion was prepared by HCl and NaOH to reach a constant pH value. The pH of the pure medium was adjusted with HCl and NaOH. After each culture medium was adjusted to a constant pH value using the method above, a constant concentration of ascorbic acid was additionally added to each culture medium. The components of the bacterial solution and each culture medium were as follows:

Bacteria solution: (*Brucella* broth 28 g/L, $NaHCO_3$ 10 g/L and 10 mM urea).

Group 1: M3V3000 (*Brucella* broth 28 g/L, 0.1 M malate buffer and 10 mM urea, pH 3.0)+(6000 mg/L Vitamin C).
Group 2: M4V3000 (*Brucella* broth 28 g/L, 0.1 M malate buffer and 10 mM urea, pH 4.0)+(6000 mg/L Vitamin C).
Group 3: M5V3000 (*Brucella* broth 28 g/L, 0.1 M malate buffer and 10 mM urea, pH 5.0)+(6000 mg/L Vitamin C).
Group 4: L3V3000 (*Brucella* broth 28 g/L, 0.1 M lactate buffer and 10 mM urea, pH 3.0)+(6000 mg/L Vitamin C).
Group 5: L4V3000 (*Brucella* broth 28 g/L, 0.1 M lactate buffer and 10 mM urea, pH 4.0)+(6000 mg/L Vitamin C).
Group 6: L5V3000 (*Brucella* broth 28 g/L, 0.1 M lactate buffer and 10 mM urea, pH 5.0)+(6000 mg/L Vitamin C).
Group 7: P3V3000 (*Brucella* broth 28 g/L, 0.1 M phosphate buffered saline (PBS) and 10 mM urea, pH 3.0)+(6000 mg/L Vitamin C).
Group 8: P4V3000 (*Brucella* broth 28 g/L, 0.1 M phosphate buffered saline (PBS) and 10 mM urea, pH 4.0)+(6000 mg/L Vitamin C).
Group 9: P5V3000 (*Brucella* broth 28 g/L, 0.1 M phosphate buffered saline (PBS) and 10 mM urea, pH 5.0)+(6000 mg/L Vitamin C).
Group 10: C3V3000 (*Brucella* broth 28 g/L, 0.1 M citrate buffer and 10 mM urea, pH 3.0)+(6000 mg/L Vitamin C).
Group 11: C4V3000 (*Brucella* broth 28 g/L, 0.1 M citrate buffer and 10 mM urea, pH 4.0)+(6000 mg/L Vitamin C).
Group 12: C5V3000 (*Brucella* broth 28 g/L, 0.1 M citrate buffer and 10 mM urea, pH 5.0)+(6000 mg/L Vitamin C).

After each culture medium incubated according to the viability check-point (0/20/40/60 minutes) was serially diluted 10 times with physiological saline, the bacteria solutions diluted at each magnification was applied to the *Brucella* solid medium for subculture by a coating method, and the coated plates were incubated at 37° C. for 72 hours in a humidified anaerobic chamber using a micro-aerobic package (Genbox microaer, BioMerieux, 96125). Finally, the viable count of each culture medium was calculated.

V. Experimental Results

Embodiment 1

The results of Embodiment 1 are shown in Table 1 and FIG. 1.

TABLE 1

| Buffer solution | Sample number | 0 | 20 | 40 | 60 | pH value measured after 60 minutes |
|---|---|---|---|---|---|---|
| | | | Time (min) Viable count ($Log_{10}$ CFU/mL) | | | |
| N (Water) | N3 | 7.18 ± 0.11 | 7.21 ± 0.13 | 7.25 ± 0.21 | 7.29 ± 0.2 | 6.01 |
| | N3V3000 | 7.34 ± 0.08 | 7.11 ± 0.09 | 6.92 ± 0.06 | 6.8 ± 0.07 | 5.13 |
| | N4 | 7.29 ± 0.12 | 7.19 ± 0.14 | 7.23 ± 0.23 | 7.27 ± 0.24 | 6.57 |
| | N4V3000 | 7.35 ± 0.08 | 7.05 ± 0.08 | 7 ± 0.09 | 7.01 ± 0.05 | 5.13 |
| | N5 | 7.31 ± 0.1 | 7.19 ± 0.13 | 7.47 ± 0.42 | 7.38 ± 0.35 | 7.45 |
| | N5V3000 | 7.34 ± 0.12 | 7.07 ± 0.12 | 7.15 ± 0.04 | 7 ± 0.02 | 6.79 |
| P (PBS) | P3 | 7.22 ± 0.09 | 7.16 ± 0.12 | 7.15 ± 0.12 | 7.32 ± 0.16 | 5.51 |
| | P3V3000 | 7.35 ± 0.08 | 6.99 ± 0.09 | 6.93 ± 0.08 | 5.63 ± 0.06 | 4.92 |
| | P4 | 7.22 ± 0.15 | 7.16 ± 0.15 | 7.28 ± 0.15 | 7.4 ± 0.22 | 6.08 |
| | P4V3000 | 7.35 ± 0.07 | 7.13 ± 0.12 | 7.12 ± 0.06 | 7.02 ± 0.04 | 5.75 |
| | P5 | 7.29 ± 0.06 | 7.23 ± 0.12 | 7.39 ± 0.31 | 7.48 ± 0.36 | 6.83 |
| | P5V3000 | 7.36 ± 0.06 | 7.12 ± 0.19 | 7.15 ± 0.07 | 7.05 ± 0.07 | 6.35 |
| C (Citrate buffer) | C3 | 7.29 ± 0.09 | 5.94 ± 0.28 | 5.28 ± 0.09 | 4.35 ± 0.05 | 4.37 |
| | C3V3000 | 7.37 ± 0.09 | 4.79 ± 0.03 | 3.86 ± 0.06 | 2.08 ± 0.43 | 4.27 |
| | C4 | 7.25 ± 0.09 | 7 ± 0.12 | 6.76 ± 0.36 | 6.7 ± 0.34 | 5.06 |
| | C4V3000 | 7.34 ± 0.1 | 6.38 ± 0.04 | 6.08 ± 0.04 | 5.14 ± 0.05 | 4.83 |
| | C5 | 7.23 ± 0.08 | 7.21 ± 0.22 | 7.26 ± 0.1 | 7.21 ± 0.22 | 6.09 |
| | C5V3000 | 7.31 ± 0.1 | 7.28 ± 0.1 | 7.31 ± 0.04 | 7.19 ± 0.04 | 5.87 |

Embodiment 2

Figure 2:
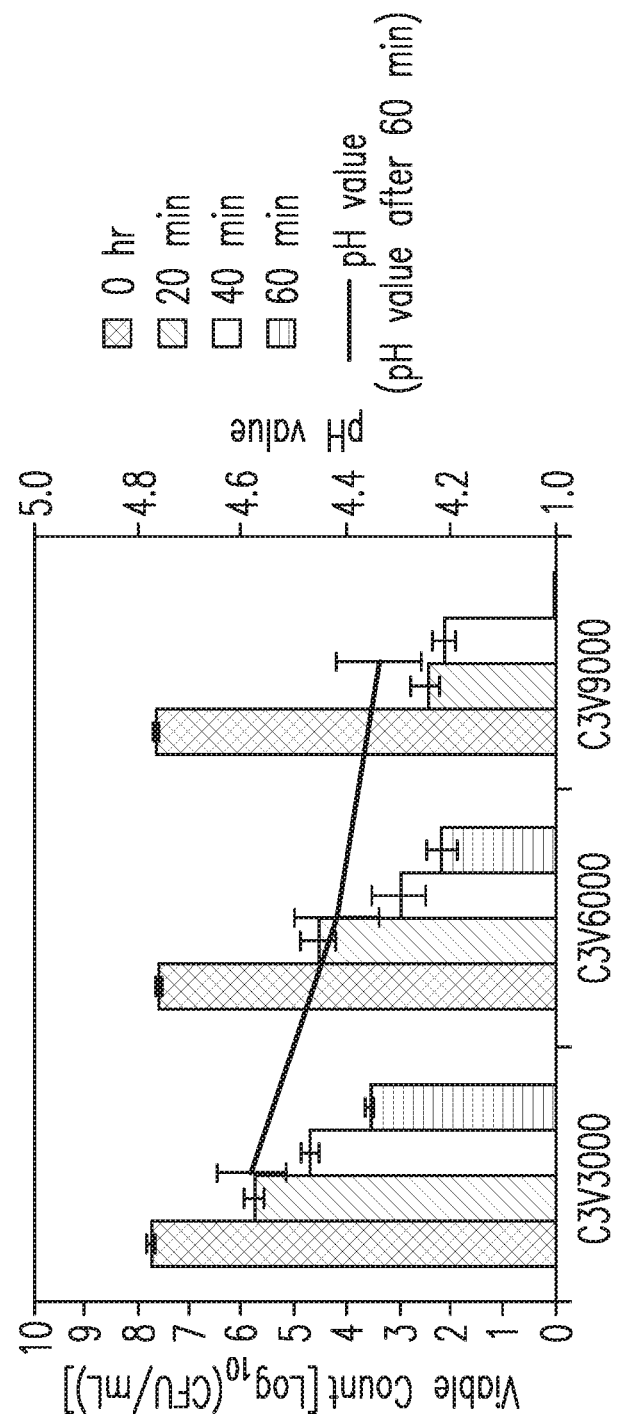
FIG. 2 is a histogram showing the results of an antibacterial experiment against *Helicobacter pylori* of the citrate buffer combination with the ascorbic acid at pH 3.0.

The results of Embodiment 2 are shown in Table 2 and FIG. 2.

TABLE 2

| Buffer solution | Sample number | 0 | 20 | 40 | 60 | pH value measured after 60 minutes |
|---|---|---|---|---|---|---|
| | | | Time (min) Viable count ($Log_{10}$ CFU/mL) | | | |
| C (Citrate buffer) | C3V3000 | 7.75 ± 0.07 | 5.77 ± 0.18 | 4.7 ± 0.18 | 3.56 ± 0.08 | 4.51 |
| | C3V6000 | 7.59 ± 0.04 | 4.56 ± 0.33 | 3.01 ± 0.51 | 2.2 ± 0.28 | 4.33 |
| | C3V9000 | 7.66 ± 0.04 | 2.5 ± 0.28 | 2.15 ± 0.21 | 0.0 ± 0.0 | 4.26 |

Embodiment 3

Figure 3:
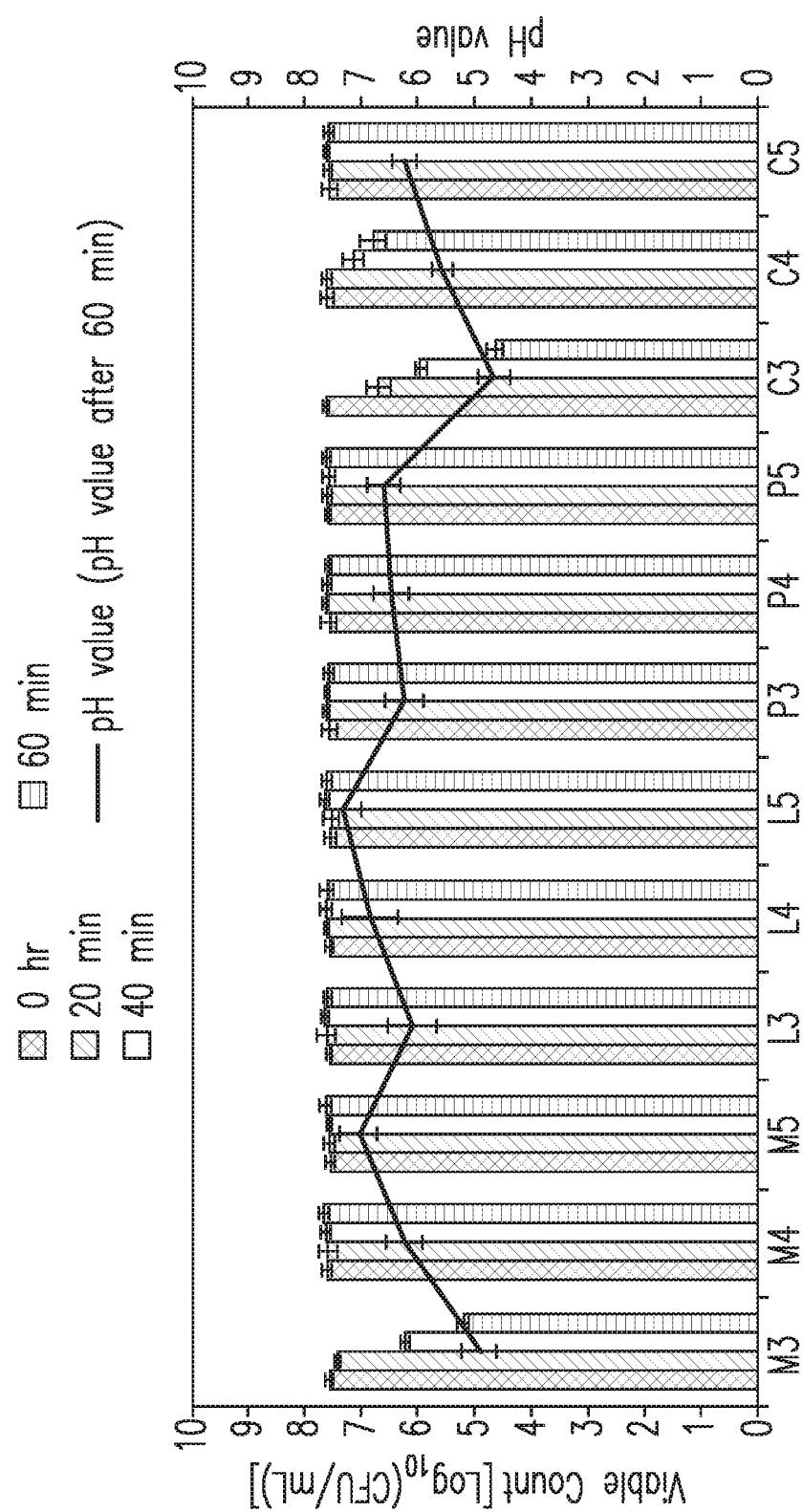
FIG. 3 is a histogram showing the results of an antibacterial experiment against *Helicobacter pylori* of the malate buffer combination, a lactate buffer combination, the citrate buffer combination and the phosphate buffer combination at pH 3.0, 4.0 and 5.0.

The results of Embodiment 3 are shown in Table 3 and FIG. 3.

TABLE 3

| Buffer solution | Sample number | 0 | 20 | 40 | 60 | pH value measured after 60 minutes |
|---|---|---|---|---|---|---|
| | | | Time (min) Viable count ($Log_{10}$ CFU/mL) | | | |
| M (Malate buffer) | M3 | 7.56 ± 0.06 | 7.42 ± 0.05 | 6.23 ± 0.08 | 5.21 ± 0.1 | 4.91 ± 0.3 |
| | M4 | 7.61 ± 0.08 | 7.59 ± 0.16 | 7.64 ± 0.08 | 7.67 ± 0.08 | 6.24 ± 0.32 |
| | M5 | 7.56 ± 0.09 | 7.58 ± 0.1 | 7.58 ± 0.04 | 7.65 ± 0.11 | 7.05 ± 0.32 |
| L (Lactate buffer) | L3 | 7.58 ± 0.05 | 7.63 ± 0.16 | 7.67 ± 0.07 | 7.62 ± 0.07 | 6.11 ± 0.42 |
| | L4 | 7.59 ± 0.06 | 7.63 ± 0.04 | 7.65 ± 0.09 | 7.64 ± 0.11 | 6.87 ± 0.48 |
| | L5 | 7.56 ± 0.1 | 7.56 ± 0.13 | 7.67 ± 0.07 | 7.64 ± 0.09 | 7.35 ± 0.32 |
| P (PBS) | P3 | 7.59 ± 0.13 | 7.64 ± 0.05 | 7.65 ± 0.04 | 7.62 ± 0.09 | 6.27 ± 0.33 |
| | P4 | 7.61 ± 0.13 | 7.66 ± 0.05 | 7.66 ± 0.08 | 7.62 ± 0.06 | 6.51 ± 0.3 |
| | P5 | 7.63 ± 0.05 | 7.65 ± 0.08 | 7.62 ± 0.11 | 7.66 ± 0.06 | 6.64 ± 0.29 |

TABLE 3-continued

| Buffer solution | Sample number | 0 | 20 | 40 | 60 | pH value measured after 60 minutes |
|---|---|---|---|---|---|---|
| | | \multicolumn{4}{c}{Viable count (Log$_{10}$ CFU/mL)} | | |
| L (Citrate buffer) | C3 | 7.66 ± 0.05 | 6.74 ± 0.22 | 5.98 ± 0.1 | 4.68 ± 0.13 | 4.69 ± 0.27 |
| | C4 | 7.66 ± 0.12 | 7.67 ± 0.09 | 7.2 ± 0.18 | 6.85 ± 0.23 | 5.61 ± 0.19 |
| | C5 | 7.61 ± 0.13 | 7.65 ± 0.07 | 7.67 ± 0.05 | 7.64 ± 0.09 | 6.29 ± 0.22 |

Embodiment 4

Figure 4:
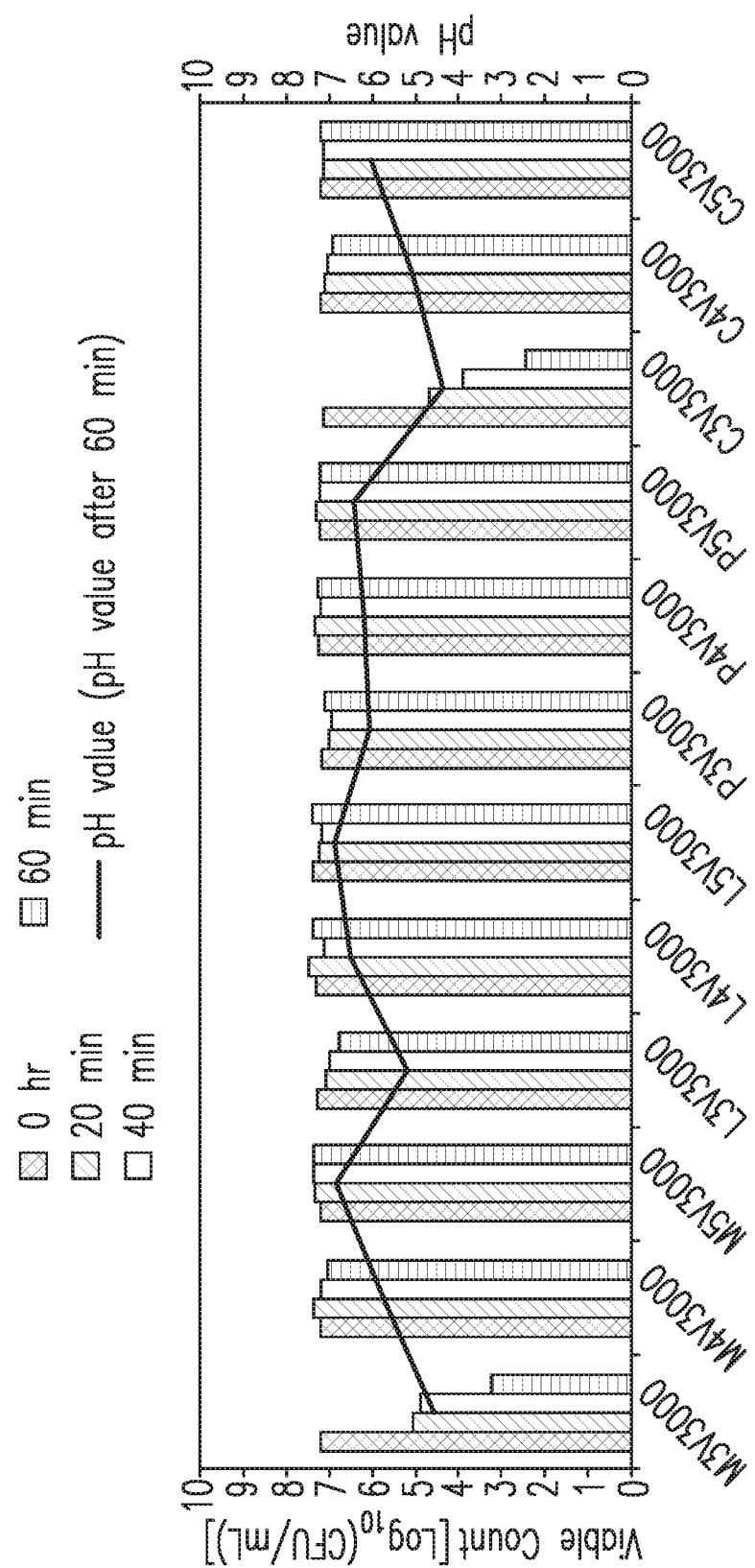
FIG. 4 is a histogram showing the results of an antibacterial experiment against *Helicobacter pylori* of the malate buffer combination with the ascorbic acid, the lactate buffer combination with the ascorbic acid, the citrate buffer combination with the ascorbic acid and the phosphate buffer combination with the ascorbic acid at pH 3.0, 4.0 and 5.0.

The results of Embodiment 4 are shown in Table 4 and FIG. 4.

TABLE 4

| Buffer solution | Sample number | 0 | 20 | 40 | 60 | pH value measured after 60 minutes |
|---|---|---|---|---|---|---|
| | | \multicolumn{4}{c}{Viable count (Log$_{10}$ CFU/mL)} | | |
| M (Malate buffer) | M3V3000 | 7.23 | 5.08 | 4.90 | 3.27 | 4.60 |
| | M4V3000 | 7.22 | 7.40 | 7.26 | 7.12 | 5.79 |
| | M5V3000 | 7.28 | 7.38 | 7.42 | 7.43 | 6.87 |
| L (Lactate buffer) | L3V3000 | 7.36 | 7.16 | 7.07 | 6.86 | 5.24 |
| | L4V3000 | 7.41 | 7.55 | 7.23 | 7.45 | 6.60 |
| | L5V3000 | 7.48 | 7.34 | 7.29 | 7.51 | 6.95 |
| P (PBS) | P3V3000 | 7.28 | 7.13 | 7.08 | 7.24 | 6.15 |
| | P4V3000 | 7.39 | 7.42 | 7.34 | 7.38 | 6.31 |
| | P5V3000 | 7.36 | 7.44 | 7.37 | 7.40 | 6.55 |
| C (Citrate buffer) | C3V3000 | 7.27 | 4.85 | 4.00 | 2.60 | 4.50 |
| | C4V3000 | 7.38 | 7.28 | 7.20 | 7.08 | 5.21 |
| | C5V3000 | 7.34 | 7.31 | 7.30 | 7.38 | 6.22 |

It can be seen from the results of Embodiment 1 that, the citrate buffer combination having a pH value below 5 of the present invention has a significant bactericidal effect in a bicarbonate environment. Normally, we take it for granted that the citric acid not only shows no bactericidal effect against *Helicobacter pylori*, but also has a diametrically opposite trend (please refer to Page 1766, left Column, Lines 26-35 and FIG. 1 in D(12), which discloses that the citric acid significantly enhances urease activity of the *Helicobacter pylori*, while the environmental pH is not a critical issue). In the present invention, the citrate buffer combination having a pH value below 5 is used as a combination component of a bactericide against *Helicobacter pylori*, which is the first time that the citric acid is used as a component for killing *Helicobacter pylori* in a bicarbonate environment with a pH value below 5, and does show a bactericidal effect, and thus the present invention displays novelty and inventiveness.

The citrate buffer combination with the ascorbic acid having a pH value below 5 demonstrates a significant "dose-dependent" bactericidal effect in the bicarbonate environment. In addition, by comparing C3 with C3V3000, and C4 with C4V3000, it can be observed that the ascorbic acid shows a significant "synergistic effect" on the sterilization of the citrate buffer combination.

Conversely, the phosphate buffer combination or water does not demonstrate bactericidal efficacy in the presence of bicarbonate. Moreover, there is neither the bactericidal effect nor the synergistic effect even when the ascorbic acid is added to the above two systems.

According to the experimental results of the Embodiment 1, the antibacterial experiment of the citrate buffer combination at pH 3 with various concentrations of the ascorbic acid was carried out in the Embodiment 2 to verify the bactericidal and the synergistic effect of the various concentrations of the ascorbic acid, and to verify the optimum concentration of bactericidal activity within 20 minutes.

Bactericidal Activity is generally defined as a 99.9% reduction in the number of colony-forming units relative to the inoculum density at a specified incubation time, which is usually 20 to 24 hours (please refer to D(13)).

It should be noted that the viable count of Embodiment 2 in FIG. 2 decreased from 7 Log$_{10}$(CFU/mL) to 3 Log$_{10}$ (CFU/mL), which achieves a bactericidal effect of 99.9%, in other words. Regarding the bactericidal synergistic effect of various concentrations of the ascorbic acid at pH 3, C3 (without the ascorbic acid) cannot effectively kill the bacteria within 60 minutes. On the other hand, C3V3000 (with 3000 mg/L of the ascorbic acid) killed the bacteria effectively within 60 minutes, C3V6000 (with 6000 mg/L of the ascorbic acid) killed the bacteria effectively within 40 minutes, and C3V9000 (with 9000 mg/L of the ascorbic acid) killed the bacteria effectively within 20 minutes as well and essentially eliminated all the bacteria within 60 minutes in fact!! The concentration of the ascorbic acid in the bactericidal composition of the present invention may be even higher as long as it meets the recommended upper limit of daily intake for the human body (up to about 2 g per day). Because the standard capacity of the buffer solution in the present invention is 1000 mL, 3000 ppm of the ascorbic acid represents 3 g of the ascorbic acid in 1000 mL of the buffer solution. Consequentially, If the actual application capacity is 200 mL, there is 0.6 g of the ascorbic acid in 200 mL of the buffer solution when the concentration of the ascorbic acid is 3000 ppm, and there is 2 g of the ascorbic acid in 200 mL of the buffer solution when the concentration of the ascorbic acid is 10,000 ppm.

Embodiment 1 and Embodiment 2 demonstrate that the citrate buffer combination with the ascorbic acid having a pH value below 5 shows a bactericidal effect in a bicarbonate environment, the bactericidal effect exhibits a "dose-dependent" relationship, and the ascorbic acid shows a significant "synergistic effect" on the bactericidal effect of the citrate buffer combination. Moreover, the bactericidal compositions of the present invention have a bigger buffer capacity for the absorption of bicarbonate ($HCO_3^-$) at pH 3 (please refer to D(14)) hence more effective in terms of sterilization.

It can be seen from the results of Embodiment 3 and Embodiment 4 that the malate buffer combination having a pH value below 5 of the present invention has a bactericidal effect in a bicarbonate environment as well. Normally, one tends to take it for granted that the malic acid not only exhibits no bactericidal effect against *Helicobacter pylori*, but also has an entirely reverse effect that both the citric acid and the malic acid enhance the urease activity of the *Helicobacter pylori* in an acid environment (please refer to Paragraph "Conclusions" in Summary and FIGS. 1-2 in D(15)). In the present invention, however, the citrate or the malate buffer combination having a pH value below 5 is used as a combination component of a bactericide against *Helicobacter pylori*, which is the first time that the citric acid or the malic acid is used as a component for killing *Helicobacter pylori* in a bicarbonate environment with a pH value below 5, and indeed it exhibits a significant bactericidal effect. Thus the present invention does show novelty and inventiveness.

In addition, by comparing Embodiment 3 and Embodiment 4, it can be observed that the ascorbic acid demonstrates a significant "synergistic effect" on the sterilization effect of the citrate or the malate buffer combination.

Conversely, the phosphate buffer combination or water does not show the bactericidal efficacy in the presence of bicarbonate, and there is neither bactericidal effect nor synergistic effect even when the ascorbic acid is added.

The citrate or the malate buffer combination having a pH value below 5 has a significant "dose-dependent" bactericidal effect associated with the ascorbic acid added in the bicarbonate environment.

The results of C3, C3V3000, C4V3000, M3, M3V3000, and M4V3000 in the embodiments demonstrate the pH value and sterilization results of the buffer combination having a pH value below 5 measured after 60 minutes can be observed.

Referring to Page 292, FIG. 3 in D(16), which shows the correlation between pH value and the ascorbate oxidase activity in *Helicobacter pylori*, there are two ascorbate oxidases in the *Helicobacter pylori*: interstitial ascorbate oxidase and endomembranous ascorbate oxidase. This correlation indicates that the two kinds of the ascorbate oxidase exhibit weak activity at pH 4-5 (please refer to FIG. 3 in D(16) mentioned above), which is advantageous for the sterilization of ascorbic acid (please also refer to paragraph [0084] and Embodiment 2 in Table 2 and FIG. 2, where the pH values after 60 minutes are kept within this range as well).

Since both the citric acid and the malic acid demonstrate an inhibitory effect on the ascorbic acid oxidase activity at pH level below 5, an advantageous environment is thus established where ascorbic acid can exhibit the synergistic effect on the disinfection significantly. On the other hand, both the phosphate buffer combination and water control groups do not exhibit such an inhibitory effect on ascorbate oxidase activity, even with the addition of the ascorbic acid (please refer to FIGS. 1-4 and Tables 1-4 of Embodiments 1, 2, 3 and 4 showing the pH values and the sterilization results measured after 60 minutes).

*Helicobacter pylori* is one of the few microorganisms that have both the urease and the ascorbate oxidase (please refer to Table 1 in D(16)), thus *Helicobacter pylori* does have a strong capability of degrading ascorbic acid. The relationship between the ascorbate oxidase of *Helicobacter pylori* and pH value is shown in FIG. 3 in D(16).

The gastric mucus gel layer becomes unfavorable to the mobility of *Helicobacter pylori* in the low pH mucus-microenvironment (please refer to the abstract in D(17)), whereas this low pH mucus-microenvironment is advantageous for the buffer composition of the present invention to sterilize and eradicate bacteria in the mucus gel layer.

While the pH value of the buffer combination of the present invention is equal to 3 at first, it goes down to less than 3 in the gastric antrum later on, which will terminate the gastric acid secretion temporarily (please refer to Page 422 in D(18) regarding pH changes), which leads to the termination of the secretion of the chloride ion accordingly. The bicarbonate secreted by the epithelial cells is subsequently inhibited temporarily as well due to this temporary termination of the chloride ion secretion in the stomach (please refer to FIG. 2 in D(19)). Thus it is even more advantageous to sterilize and eradicate bacteria under the actual condition mentioned above.

The actually obtainable pKa of the citric acid is 3.1 in practice, and the standard pKa of the citric acid is 3.12 in literature (please refer to D(14)). Therefore the citrate buffer combination exhibits an even bigger buffer capacity for the absorption of bicarbonate ($HCO_3^-$) at pH level equal to 3 as compared with other buffer combinations we have prepared.

Therefore, it is crucial to set the pH value equal to 3 in order to effectively sterilize and eradicate bacteria. The buffer capacity presented at this pH condition is also critical. Moreover, it is also crucial to inhibit ascorbate oxidase activity effectively at this pH condition! The addition of the ascorbic acid at this pH condition is the most critical factor for rapid sterilization (synergistic effect). For experiments conducted at pH level equal to 3, although the original pH at the start of Embodiments 1, 2, 3 and 4 are set to 3, the actual pH level of the citrate or the malate buffer combination with ascorbic acid added in the mucus-microenvironment tends to approach a level below 5 eventually, which proves to be beneficial for sterilizing and eradicating bacteria.

The pH value of the citrate or the malate buffer combination (pH=3) in the present invention in the gastric antrum can be adjusted by the detailed composition of the buffer with a goal to keep it less than 3 in practice in order to maintain the low pH environment in the gastric antrum (please refer to FIG. 1 in D(20)), which is beneficial in inhibiting the gastric acid secretion (i.e. inhibiting chloride ion secretion). The gastric acid secretion is inhibited when the pH value in the gastric antrum is less than 3, which is similar to the functions of antacids or PPI, but the pH change of the present invention is different from that of the antacid or PPI because the present invention does not lead to a significant increase of pH value above 6 (please refer to reference D(18)), and the normally continuous secretion of bicarbonate by the epithelial cells is temporarily inhibited as a result. This is advantageous for the citrate or the malate buffer composition in the present invention to sterilize and eradicate bacteria in a low pH mucus-microenvironment.

The concentration of bicarbonate ($HCO_3^-$) secreted by the epithelial cells in the gastric mucus gel layer is positively correlated with the concentration of chloride ions in the stomach (please refer to FIG. 4 in D(21)).

In the Embodiments 1, 2, 3, and 4, the key outcome to be noted is "the pH value after 60 minutes", which indicates the pH value variation of the mucoepithelial interface with time.

In the present invention, particularly in the Embodiments 2, the citrate buffer combination alone and the citrate buffer combination with the ascorbic acid added, are capable of sterilizing and eradicating bacteria, with the former sterilizes bacteria within 60 minutes, and the latter disinfects bacteria within 20 minutes. The amount of sodium bicarbonate ($NaHCO_3$) added demonstrates the pH value in the mucoepithelial interface after 60 minutes. Moreover, it also represents the required buffer capacity of the present invention which can absorb bicarbonate ($HCO_3^-$) effectively to keep the pH value of the mucus-microenvironment below 5 in 60 minutes.

Based on the Embodiments 1, 2 and 4 above, it appears that the ascorbic acid has the functions of repairing and protecting the gastric mucus gel layer (please refer to the abstract in D(22)) as well as the mucolytic property (please refer to the abstract in D(23)) in the present invention. Moreover, the ascorbic acid demonstrates a significant effect of rapid sterilization and a significant synergistic effect on the citrate or the malate buffer combination alone. The gastric antrum inhibits gastric acid secretion when pH below 3 (please refer to Page 422 in D(18) regarding pH changes), which is advantageous to sterilize and eradicate bacteria. C3V9000 (the citrate buffer combination with the ascorbic acid at pH 3) can eradicate the *Helicobacter pylori* completely within 60 minutes, which is a preferred sterilization combination.

Regarding the increasing antibiotic resistance of the *Helicobacter pylori*, the buffer composition of the present invention (the ascorbic acid combined with the citrate or the malate buffer combination) is a bactericidal combination from nature rather than synthesized artificially. The antibiotic resistance of the *Helicobacter pylori* is due to the ability of *Helicobacter pylori* to develop antibiotic resistance via gene exchange or chromosomal mutation (please refer to D(24) and D(25)). The *Helicobacter pylori* naturally undergoes gene mutation during replication. If antibiotics are used during this process, it tends to generate antibiotic-resistant mutants (please refer to D(24) and D(25)). The *Helicobacter pylori* will divide and multiply in the environment of pH 6-8, this environment is also the optimum pH environment for antibiotics to kill the bacteria effectively (please refer to (D5)), and thus it seems to be the main cause of the increasing antibiotic resistance of *Helicobacter pylori*. The buffer composition of the present invention (the ascorbic acid combined with the citrate or the malate buffer combination) sterilizes bacteria mainly in the environment at pH of 3, hence the *Helicobacter pylori* does not divide and multiply in this low pH environment in general, therefore it is less likely to generate an antibiotic-resistance mutant.

As the non-pharmaceutical bactericidal composition of the present invention does not contain any antibiotic component, there should be no concerns of drug resistance and food safety in principle when used as a medicine for human beings.

It is understood, that the present invention is not limited to the particular embodiments disclosed, but is intended to cover all modifications which are within the spirit and scope of the invention as defined by the appended claims, the above description, and/or shown in the attached drawings.

Embodiments

1. A non-pharmaceutical bactericidal composition against a *Helicobacter pylori* including a first daily edible component, a second daily edible component, a salt and a third daily edible component, wherein the first daily edible component has a molecular state and a dissociated state while in an aqueous solution state, the first daily edible component of the molecular state is used for performing functions of killing the *Helicobacter pylori* and inhibiting an ascorbate oxidase activity of the *Helicobacter pylori* in an environment with a pH value below 5, and the first daily edible component is a citric acid, a malic acid or a combination thereof, wherein the second daily edible component is used for neutralizing a bicarbonate and being a citric acid, a malic acid or a combination thereof, wherein the salt is used to form a buffer combination with the citric acid, the malic acid or the combination thereof, the salt is a salt of the citric acid, a salt of the malic acid or a combination thereof, and wherein the third daily edible component is used for killing the *Helicobacter pylori* more thoroughly in the presence of the first daily edible component, the second daily edible component and the salt, and the third daily edible component is an ascorbic acid.

2. The non-pharmaceutical bactericidal composition according to Embodiment 1, wherein the ascorbic acid has a concentration being in a range from 3000 ppm to 10000 ppm.

3. The non-pharmaceutical bactericidal composition according to one of Embodiment 1 and 2, wherein the ascorbic acid has a concentration of 9000 ppm.

4. The non-pharmaceutical bactericidal composition according to any one of Embodiments 1 to 3, wherein the salt is a sodium citrate, a sodium malate or a combination thereof.

5. A non-pharmaceutical bactericidal composition against a *Helicobacter pylori*, including a first daily edible component and a second daily edible component, wherein the first daily edible component is a buffer combination consisting of an organic acid and a salt of the organic acid, the first daily edible component is used for neutralizing a bicarbonate and performing functions of killing the *Helicobacter pylori* and inhibiting an ascorbate oxidase activity of the *Helicobacter pylori* in an environment with a pH value below 5, and the organic acid is a citric acid, a malic acid or a combination thereof, and wherein the second daily edible component is used for killing the *Helicobacter pylori* more thoroughly in presence of the first daily edible component, and the second daily edible component is an ascorbic acid.

6. The non-pharmaceutical bactericidal composition according to Embodiments 5, wherein the non-pharmaceutical bactericidal composition has a pH value below 5.

7. The non-pharmaceutical bactericidal composition according to one of Embodiments 5 and 6, wherein the non-pharmaceutical bactericidal composition has a pH value being in a range from 3 to 5.

8. The non-pharmaceutical bactericidal composition according to any one of Embodiments 5 to 7, wherein the non-pharmaceutical bactericidal composition has a pH value of 3.

9. A non-pharmaceutical bactericidal composition against a *Helicobacter pylori* including a first daily edible component and a second daily edible component, wherein the first daily edible component has a molecular state and a dissociated state while in an aqueous solution state, the first daily edible component of the molecular state is used for performing functions of killing the *Helicobacter pylori* and inhibiting an ascorbate oxidase activity of the *Helicobacter pylori* in an environment with a pH value below 5, and the first daily edible component is a citric acid, a malic acid or a combination thereof, and wherein the second daily edible component is a salt used to form a buffer combination with the first daily edible component, and used to neutralize a bicarbonate, so that the first daily edible component can continue its killing of the *Helicobacter pylori* effectively and inhibiting the ascorbate oxidase activity of the *Helicobacter pylori*, and the salt is a salt of the citric acid, a salt of the malic acid or a combination thereof.

10. The non-pharmaceutical bactericidal composition according to Embodiments 9, wherein the non-pharmaceutical bactericidal composition has a pH value of 3.

11. The non-pharmaceutical bactericidal composition according to one of Embodiments 9 and 10, wherein the salt is a sodium citrate, a sodium malate or a combination thereof.

12. The non-pharmaceutical bactericidal composition according to any one of Embodiments 9 to 11, further including an ascorbic acid for killing the *Helicobacter pylori* more thoroughly in presence of the first daily edible component and the second daily edible component.

13. A method for treating a *Helicobacter pylori* infection, including steps of providing a non-pharmaceutical bactericidal composition including a first daily edible component and a second daily edible component, and administering the non-pharmaceutical bactericidal composition to a mammal, wherein the first daily edible component has a molecular state and a dissociated state while in an aqueous solution state, the first daily edible component of the molecular state is used for performing functions of killing a *Helicobacter pylori* and inhibiting an ascorbate oxidase activity of the *Helicobacter pylori* in an environment with a pH value below 5, the first daily edible component is a citric acid, a malic acid or a combination thereof, and the second daily edible component is a salt, is used to form a buffer combination with the first daily edible component, and is used to neutralize a bicarbonate, so that the first daily edible component can continue its killing of the *Helicobacter pylori* effectively and inhibiting the ascorbate oxidase activity of the *Helicobacter pylori*, and the salt is a salt of the citric acid, a salt of the malic acid or a combination thereof.

14. The method according to Embodiment 13, wherein the ascorbic acid has a concentration being in a range from 3000 ppm to 10000 ppm.

15. The method according to one of Embodiments 13 and 14, wherein the ascorbic acid has a concentration of 9000 ppm.

16. The method according to any one of Embodiments 13 to 15, wherein the non-pharmaceutical bactericidal composition has a pH value below 5.

17. The method according to any one of Embodiments 13 to 16, wherein the non-pharmaceutical bactericidal composition has a pH value being in a range from 3 to 5.

18. The method according to any one of Embodiments 13 to 17, wherein the non-pharmaceutical bactericidal composition has a pH value of 3.

19. The method according to any one of Embodiments 13 to 18, wherein the non-pharmaceutical bactericidal composition further includes an ascorbic acid for killing the *Helicobacter pylori* more thoroughly in presence of the first daily edible component and the second daily edible component.

20. The method according to any one of Embodiments 13 to 19, wherein the mammal is a human being.

What is claimed is:

1. A method for treating a *Helicobacter pylori* infection in gastric mucus with the presence of bicarbonate ion and urea, the method comprising steps of:

providing a non-pharmaceutical bactericidal composition including:
a first daily edible component having a molecular state and a dissociated state while in an aqueous solution state, wherein the first daily edible component of the molecular state is used for performing functions of killing a *Helicobacter pylori* and inhibiting an ascorbate oxidase activity of the *Helicobacter pylori* in an environment with a pH value below 5 with the presence of the bicarbonate ion and the urea, the first daily edible component is a citric acid, a malic acid or a combination thereof;
a second daily edible component, being a salt, used to form a buffered combination having a buffer pH value below 5 with the first daily edible component, and used to neutralize the bicarbonate ion, so that the first daily edible component can continue its killing of the *Helicobacter pylori* effectively and inhibiting the ascorbate oxidase activity of the *Helicobacter pylori* so as to enable a synergistic effect of an ascorbic acid on a bactericidal effect of the buffered combination, wherein the salt is a salt of the citric acid, a salt of the malic acid or a combination thereof; and
a third daily edible component being the ascorbic acid, wherein the ascorbic acid has a concentration being in a range from 3000 ppm to 10000 ppm and shows the synergistic effect on the bactericidal effect of the buffered combination; and
administering the non-pharmaceutical bactericidal composition to a mammal wherein the *Helicobacter pylori* is eliminated within 60 minutes.

2. The method as claimed in claim 1, wherein the ascorbic acid has the concentration of 9000 ppm, which achieves $IC_{99}$ of the *Helicobacter pylori* within 20 minutes.

3. The method as claimed in claim 1, wherein the buffer pH value is in a range from 3 to 5.

4. The method as claimed in claim 1, wherein the buffer pH value is 3.

5. The method as claimed in claim 1, wherein the mammal is a human being.

6. The method as claimed in claim 1, wherein the synergistic effect includes an effect of rapid sterilization so as to kill the *Helicobacter pylori* effectively.

7. The method as claimed in claim 1, wherein the buffered combination has a dose-dependent relationship with the concentration of the ascorbic acid added in the environment.

* * * * *